United States Patent [19]

Ohkura

[11] Patent Number: 4,705,757

[45] Date of Patent: Nov. 10, 1987

[54] METHOD FOR FLUOROMETRIC ANALYSIS OF CATECHOL AMINES

[75] Inventor: Yosuke Ohkura, Fukuoka, Japan

[73] Assignee: Toyo Soda Manufacturing Co., Ltd., Shinnanyo, Japan

[21] Appl. No.: 717,664

[22] Filed: Mar. 29, 1985

[30] Foreign Application Priority Data

Mar. 29, 1984 [JP] Japan ................................. 59-62890

[51] Int. Cl.$^4$ ...................... G01N 21/76; G01N 33/00
[52] U.S. Cl. ..................................... 436/172; 436/89; 436/111; 436/129; 436/131
[58] Field of Search ................... 436/172, 111, 89, 90, 436/129, 131

[56] References Cited

U.S. PATENT DOCUMENTS

| 4,045,487 | 8/1977 | Cleeland, Jr. et al. | 436/172 X |
| 4,311,790 | 1/1982 | Vlachakis | 436/131 X |
| 4,419,452 | 12/1983 | Imai et al. | 436/96 X |
| 4,420,565 | 12/1983 | Schmitt | 436/27 |
| 4,432,907 | 2/1984 | Wieder et al. | 436/56 X |

OTHER PUBLICATIONS

Caidi (15):123155r, Nohta et al., Bunseki Kagaku, 33(7), E263–E269, 1984.

L. D. Mell et al.: Journal of Liquid Chromatog., 1(3), 261–77 (1978).
A. H. Anton et al.: J. Pharmacol. Exp. Ther., 138, 360–75 (1962).
A. Yamatodani et al.: Clin. Chem., 27, 1983-87 (1981).
P. T. Kissinger et al.: Biochem. Med., 13, 299–306 (1975).
T. Seki: J. Chromatogr., 155, 415–420 (1977).
K. Imai et al.: Clin. Chim. Acta, 85, 1–6(1977).
Y. Yui et al.: Clin. Chem., 26, 194–196 (1980).
T. P. Moyer et al.: Clin. Chem., 25, 256–263 (1979).
D. F. Sharman: British Medical Bulletin, 29, 110–115 (1973).
R. W. Frei et al.: J. Liq. Chromatogr., 1, 443–455 (1978).

Primary Examiner—Barry S. Richman
Assistant Examiner—Lynn M. Kummert
Attorney, Agent, or Firm—Oblon, Fisher, Spivak, McClelland & Maier

[57] ABSTRACT

A method for fluorometric analysis of catecholamines characterized in that, after the addition of a catecholamine into a solution of 1,2-diphenylethylenediamine containing an oxidizing reagent at a pH of 4 to 10, the mixture is allowed to stand for more than 1 minute at a temperature of higher than 15° C. to make cateocholamine fluorescent, is disclosed.

20 Claims, 1 Drawing Figure

METHOD FOR FLUOROMETRIC ANALYSIS OF CATECHOL AMINES

BACKGROUND OF THE INVENTION

1. Field of the Invention

The present invention relates to a method for fluorometric analysis for catecholamine using 1,2-diphenylethylenediamine.

2. Discussion of the Background

Catecholamine is a general term of biogenic amines having a 3,4-dihydroxyphenyl group. In particular, catecholamines such as norepinephrine, epinephrine, dopamine and the like which are metabolites of tyrosine are performing an important function as the adrenal medulla hormones or as the neurotransmittors at the end of the sympathetic nerves. Therefore, the analysis of catecholamine is indispensable for the studies of the endocrinium and the nervous system. However, the content of catecholamine is extremely low in the tissue; it is no more than $1/10^4$ of amino acid, so the analytical method with high sensitivity is required. Recently, high sensitivity fluorometric analysis of catecholamine attracted attention as a clinical application.

Although there is a method for measuring the native fluorescence of catecholamine at pH 1, it is not specific for catecholamine and the sensitivity is not so high. One method which is adopted most popularly is to determine the fluorescence of trihydroxyindole (THI) formed by treating catecholamine with the oxidizing agent. This method has high sensitivity particularly to norepinephrine and epinephrine. But, dopamine, is resistant to the oxidation and its detection cannot be achieved with sufficient sensitivity even by the THI method. Another method is also known which determines catecholamine through the condensation reaction with ethylenediamine, but it has shortcomings in that the procedure is complicated and the sensitivity is low.

SUMMARY OF THE INVENTION

As a result of diligent investigations aiming at the development of a high sensitive fluorescence derivatizing reagent for biological catecholamine, the inventors have found that 1,2-diphenylethylenediamine (hereinafter abbreviated as DPE) reacts with catecholamine to give a strongly fluorescing compound leading to the completion of the invention.

Namely, the invention provides a method for fluorometric analysis of catecholamines using DPE as a fluorescence-derivatizing reagent, wherein, after the addition of catecholamine into a solution of DPE containing an oxidizing agent at pH 4 to 10, the mixture is allowed to stand for more than 1 minute at a temperature of higher than 15° C. to make catecholamine fluorescent.

DETAILED DESCRIPTION OF THE PREFERRED EMBODIMENTS

Figure 1:
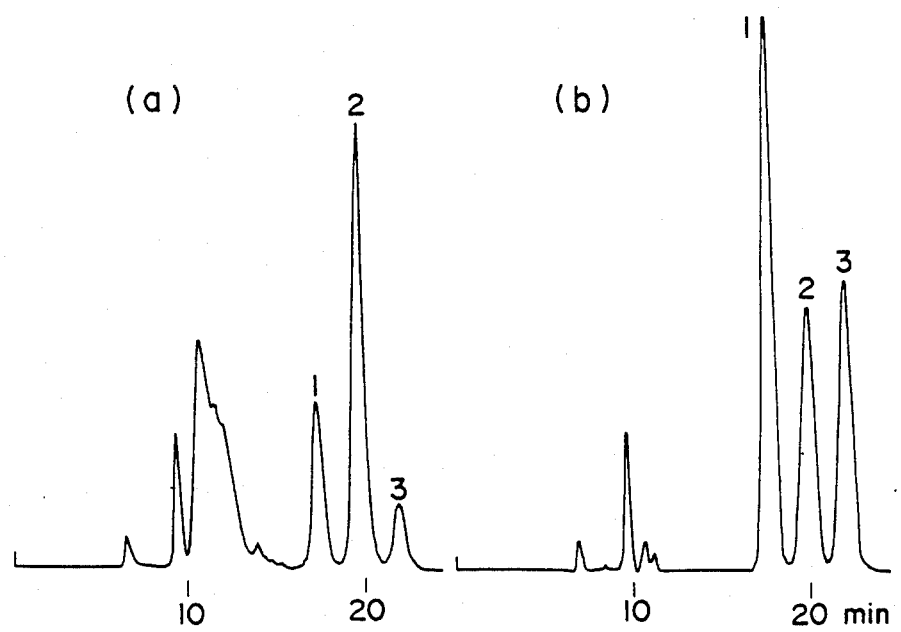
FIGS. 1a and b are chromatograms of serum and standard sample measured according to the invention, respectively.
1.=Epinephrine
2.=Norepinephrine
3.=Dopamine.

The synthesis of DPE of the invention is conducted as follows: To N-benzyl-N'-benzylidene-meso-1,2-diphenylethylenediamine obtained by refluxing ammonium acetate and benzaldenyde for several hours are added water and concentrated sulfuric acid. After allowing the mixture to react by heating and by passing steam through the reaction mixture for several hours, the mixture is neutralized and cooled with ice. Thereby, crystals of DPE can be obtained easily (J. Inorg. Nucl. Chem, 27, (1965) 270–271).

The concentration of DPE to the reaction is higher than 10 mM, preferably 0.1 to 0.3M. The concentration not higher than 10 mM is not preferable because of a rapid decrease of reaction rate. Practically, a concentration of 0.1 to 0.3M is preferable where high reaction rate is obtainable.

Since the solution of DPE is a strong base, the pH value of the solution of DPE containing the oxidizing reagent is adjusted to pH 4 to 10, preferably to pH 5 to 9 acid addition.

As the acids, inorganic acids such as hydrochloric acid, nitric acid, etc. and organic acids such as formic acids, acetic acid, etc. can be utilized, but hydrochloric acid and acetic acid are particularly preferable. Moreover, Bicine, Britton-Robinson buffer solution, etc. may be used safely to keep the pH value constant.

At pH not higher than 4, the reaction does not take place or the reaction rate is low, and, in a high pH range over 10, the reaction velocity decreases, so this range is not preferable. Practically, a range of pH 5 to 9 is preferable where the reaction velocity takes maximum value.

As oxidizing reagents which can be used, potassium ferricyanide, sodium hypochlorite, hydrogen peroxide, oxygen, etc. can be utilized, but potassium ferricyanide is particularly preferable. The concentration of the oxidizing reagent should be higher than 0.5 mM, preferably 1.8 to 3.0 mM. A concentration of the oxidizing reagent below 0.5 mM is not preferable since the reaction rate is low and sufficient reaction does not take place. Moreover, in a concentration range over 0.5 mM, the reaction rate decreases gradually with an increase in the concentration, but a range of 1.8 to 3.0 mM is preferable where the maximum and constant value is obtainable.

The reaction temperature should be higher than 15° C., preferably 30° to 100° C., and the period of time for allowing to stand is more than 5 minutes, preferably 10 to 40 minutes. At temperatures below 15° C., the reaction rate is low and it takes a long time to reach the maximum value, and, in a range of standing time of not more than 5 minutes, the reaction does not progress sufficiently, so neither range is preferable.

The fluorescent body obtained through the reaction mentioned above is stable for 2 hours at least.

Moreover, in the aforementioned reaction, in the presence of a catalyst in DPE solution containing oxidizing reagent, the reaction proceeds much faster.

Ordinary oxidation promoters can be used without any trouble. Among them, glycine, ethanol, acetonitrile and acetone are preferable, but glycine is particularly preferable.

The oxidation promoter is used at a concentration greater than 0.05M, preferably 0.2 to 0.8M. A concentration of oxidation promotor below 0.05M is not preferable since the reaction rate is low and sufficient reaction does not take place. Practically, a range of 0.2 to 0.8M is preferable where the reaction rate is high.

As described above, according to the invention, the fluorescence-tagged substance of the catecholamines can be obtained easily using DPE as a fluorescence derivatizing agent. Therefore, this is applicable not only to the manual method, but also to the precolumn or postcolum derivatizing methods of high performance liquid chromatography, and can be said to be an excellent method of wide application for fluorescent analysis.

pamine, about 500 times as strong fluorescences were observed as those by THI method showing the method of the invention to have high sensitivity. No DPE did react with the biological constituents such as sugars, keto acids, amino acids, nucleic acid bases, steroids, polyaminocarboxylic acis, alcohols and aldehydes, and was confirmed to be a selective reagent for catecholamines.

TABLE 1

| | Fluorescence characteristic and limit of detection of catechol compounds reacted with DPE | | | |
|---|---|---|---|---|
| Catechol compound | Excitation wavelength λex(nm) | Fluorescence wavelength λem(nm) | Relative intensity of fluorescence | Limit of detection pmol/ml |
| catechol | 345 | 480 | 14 | 100 |
| Pyrogallol | 330 | 475 | 3 | 500 |
| 3,4-Dihydroxybenzylamine | 340 | 470 | 32 | 50 |
| 3,4-Dihydroxybenzoic acid | 330 | 480 | 3 | 500 |
| Norepinephrine | 340 | 480 | 100 | 15 |
| Epinephrine | 350 | 496 | 64 | 20 |
| Dopamine | 347 | 470 | 84 | 20 |
| Isoproterenol | 356 | 497 | 104 | 10 |
| Dopa | 348 | 480 | 19 | 80 |
| 3,4-Dihydroxyphenyl | 345 | 477 | 72 | 20 |
| 3,4-Dihydroxymandelic acid | 350 | 470 | 9 | 150 |
| 3,4-Dihydroxyphenylethylene glycol | 347 | 478 | 95 | 15 |
| 2-Hydroxyestrone | 350 | 475 | 6 | 300 |
| 4-Hydroxyestrone | 350 | 475 | 1 | 1800 |

In following, the invention will be illustrated more completely using examples.

EXAMPLE 1

The manual fluorometric determination was investigated using norepinephrine, epinephrine, dopamine isoproterenol. DPE was synthesized by the method shown below.

N-benzoyl-N'-benzylidene-meso-1,2-diphenylethylenediamine is obtained in a yield of 44% by refluxing together for 3 hours 40 g of ammonium acetate and 100 ml of benzaldehyde, 10 g of N-benzyl-N'-benzylidenemeso-1,2-diphenylethylenediamine, 100 ml of water and 54 ml of concentrated sulfuric acid were combined and, and the mixture was allowed to react for 4 hours by heating and by passing steam through the reaction mixture. After completion of the reaction, the mixture was neutralized with ammonia and cooled with ice to obtain crystals of 1,2-diphenylethylenediamine.

To a solution of DPE made by adding 20 ml of 0.05M Bicine buffer solution (pH 7.0) containing 0.5M glycine, 0.1 ml of 0.1M DPE solution (ethanol solvent) and 0.1 ml of 2.5 mM potassium ferricyanide solution sequentially various types of catecholamines were added. After standing for 30 minutes at 37° C., the fluoroscence intensity was measured. The optimal wavelength of the fluorescence defection is shown in Table 1. The lower limit of the determination (S/N=2) was $2 \times 10^{-8}$M for all of catecholamines. Moreover, when simultaneous measurements were made twenty times using $1 \times 10^{-6}$M solution, the coefficient of variation was found to be 1% or so for all catecholamines. DPE reacted selectively only with the compounds having a skeleton of catechol as shown in Table 1, and there were no significant differences in the intensity of fluorescence among norepinephrine, epinephrine, dopamine and isoproterenol. When compared with the THI method in which the fluorescence of trihydroxy-indole formed by treating catecholamine with oxidizing agent is measured, in regard to norepinephrine, epinephrine and isoproterenol, about 10 times and, in regard to do-

EXAMPLE 2

The manual, determination of the fluorescence was investigated using norepinephrine, epinephrine, dopamine and isoproterenol.

To 20 ml of a solution made by adding acid to 0.005M 1,2-diphenylethylenediamine to adjust the pH to 7.0 were added 2.5 mM of potassium ferricyanide. After allowing the mixture to stand for 30 minutes at 70° C., the fluorescence was measured. The optimal wavelength for the fluorescence measurement was shown in Table 1. The limit of the detection (S/N=2) was $8 \times 10^{-8}$M for all of catecholamines. Moreover, when simultaneous measurements were made twenty time using $1 \times 10^{-6}$M solution, the coefficient of variation was found to be 1% or so for all of catecholamines.

EXAMPLE 3

When many constituents are present in the biological samples etc., the high-performance liquid chromatography (HPLC) is powerful as a method for the analysis. Therefore, the analysis of catecholamines were carried out by the precolumn derivatizing method using DPE.

To the sample solution (1.0 ml) were added 2.0 ml of 0.05M Bicine buffer solution (pH 7.0) containing 0.5M glycine, 0.1 ml of 0.1M DPE solution (ethanol solvent) and 0.1 ml of 0.08% (W/V) potassium ferricyanide solution in sequence. After allowing to stand for more than 30 minutes at 37° C., 100 μl of the reaction liquid were injected into HPLC apparatus. Conditions of HPLC were as follows: column; Ultrasphere-ODS (4.6ϕ×150 mm, Beckman), eluate; CH₃CN—H₂O (47.5:52.5 W/V), flow rate 1 ml/min. For the fluorescence detection, Shimazu FLD-I (excitation 300–400 nm, fluorescence 450–800 nm) was employed. Under these conditions, reversed-phase partition type column as mentioned above, norepinephrine, epinephrine and isoproterenol gave a single peak respectively. Although dopamine gave two peaks of an intensity ratio of 9:1, the determination was possible with either of them. The elution was completed within 12 minutes, and the lower limit of detection was 10 pg at S/N ratio of 2.

EXAMPLE 4

The precolumn derivatizing method which allows reaction prior to the injection into HPLC as in Example 3 necessitates a complicated procedure and is troublesome because of the manual practice of the reaction. Therefore, more powerful analysis of catecholamine was carried out which is automatable by the post-column derivatizating method allowing development after the separation with HPLC.

Into the column eluate, containing (1) (TSK-gel Ether 250, Tōyō Soda Kōgyō Co., Ltd.) 10 mM of sodium acetate, 30 mM of sodium perchlorate and 5% ethanol was injected the biological sample. After allowed catecholamine to absorb to the column (1), this was washed with purified water. Then, the catecholamine constituents were transferred to the column (2) (TSK-gel SP-2SW, Tōyō Soda Kōgyō Co., Ltd.) with aqueous solution of 20 mM sodium acetate/acetonitrile=50/50. Following this, catecholamine was separated into three constituents in the column (3) (TSK-gel Catecholpak, Tōyō Soda Kōgyō Co., Ltd.) using aqueous solution of 0.2M sodium chloride containing 10% acetonitrile as an eluate for HPLC. These three separated constituents were mixed with aqueous solution of 0.01M DPE/ethanol=50/50 and aqueous solution of 0.5 mM potassium ferricyanide/ethanol=50/50, and made up the fluorescence emitting constituents in the reaction coil. These fluorescence-emitting constituents were detected by the use of fluorescence detector (FS-8000, Tōyō Soda Kōgyō Co., Ltd.).

FIG. 1 shows the chromatograms of the standard sample (each 100 pg/ml) and the serum sample measured. The limit of the detection is 2 pg at SN ration of 2.

What is claimed is:

1. A method for the fluorometric analysis of catecholamines in a liquid sample comprising the steps of: adding to a liquid sample containing a catecholamine a solution of 1,2-diphenylethylenediamine containing an oxidizing agent at pH 4 to 10 to form a mixture, permitting the mixture to stand for more than 1 minute at a temperature higher than 15° C. and up to 100° C., to make the catecholamine fluorescent, and measuring resulting fluorescence.

2. The method for fluorometric analysis of catecholamines described in claim 1, wherein the solution of 1,2-diphenylethylene diamine in combination with an oxidation promoter.

3. A method for the fluorometric analysis of a catecholamine, comprising:
    (i) adding a catecholamine to a solution of 1,2-diphenylethylenediamine containing an oxidizing agent, at a pH 4 to 10 to form a mixture;
    (ii) permitting the mixture to stand for more than 1 minute at a temperature greater than 15° C. to make the catecholamine fluorescent; and
    (iii) measuring resulting fluorescence.

4. The method of claim 3, comprising using a solution of 1,2-diphenylethylenediamine in combination with an oxidation promoter.

5. The method of claim 3, comprising using as an oxidizing agent potassium ferricyanide, sodium hypochlorite, hydrogen peroxide or oxygen.

6. The method of claim 3, comprising using as an oxidizing agent potassium ferricyanide.

7. The method of claim 3, comprising using the oxidizing agent in a concentration greater than 0.5 mM.

8. The method of claim 3, comprising using the oxidizing agent in a concentration of from 1.8 to 3.0 mM.

9. The method of claim 3, wherein the temperature is from 30° to 100° C.

10. The method of claim 3, comprising permitting the mixture to stand for more than 5 minutes.

11. The method of claim 3, comprising permitting the mixture to stand for 10 to 40 minutes.

12. The method of claim 3, comprising using a 1,2-diphenylethylenediamine concentration greater than 10 mM.

13. The method of claim 12, comprising using a 1,2-diphenylethylenediamine concentration of from 0.1 to 0.3M.

14. The method of claim 3, comprising using a buffer to keep the pH value constant.

15. The method of claim 14, comprising using a Bicine buffer or a Britton-Robinson buffer.

16. The method of claim 3, comprising using an oxidation catalyst.

17. The method of claim 16, comprising using glycine, ethanol, acetonitrile or acetone as the catalyst.

18. The method of claim 3, comprising using a pH of from 5 to 9.

19. The method of claim 18, comprising obtaining a pH of 4 to 10 by the addition of an acid, said acid comprising hydrochloric acid, nitric acid, formic acid, or acetic acid.

20. The method of claim 19, comprising using hydrochloric acid or acetic acid.

* * * * *